US00PP30574P2

(12) United States Plant Patent
Kordes

(10) Patent No.: US PP30,574 P2
(45) Date of Patent: Jun. 18, 2019

(54) MINIATURE ROSE PLANT NAMED 'KORPOT083'

(50) Latin Name: *Rosa hybrida*
Varietal Denomination: KORpot083

(71) Applicant: W. KORDES' SÖHNE Rosenschulen GmbH & Co., KG, Klein Offenseth-Sparrieshoop (DE)

(72) Inventor: Wilhelm-Alexander Kordes, Klein Offenseth-Sparrieshoop (DE)

(73) Assignee: W. KORDES' SOHNE ROSENSCHULEN GMBH & CO. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/732,588

(22) Filed: Nov. 30, 2017

(30) Foreign Application Priority Data

Oct. 18, 2017 (QZ) ..... PBR 2017/2620

(51) Int. Cl.
*A01H 5/02* (2018.01)

(52) U.S. Cl.
USPC ..... Plt./116
CPC ..... *A01H 5/02* (2013.01)

(58) Field of Classification Search
USPC ..... Plt./116, 123
CPC ..... A01H 5/0222
See application file for complete search history.

(56) References Cited

U.S. PATENT DOCUMENTS

PP18,840 P2 5/2008 Kordes

*Primary Examiner* — Kent L Bell
(74) *Attorney, Agent, or Firm* — Buchanan Ingersoll & Rooney PC

(57) ABSTRACT

A new and distinct variety of Miniature Rose Plant, herein referred to by its cultivar name, 'KORpot083', is provided which forms in abundance on a substantially continuous basis attractive, red and white striped colored blossoms. The vegetation is vigorous and the growth habit is compact. Attractive ornamental foliage is formed with good disease resistance. The new variety is particularly well suited for providing distinctive ornamentation in the landscape.

1 Drawing Sheet

CROSS-REFERENCE TO RELATED APPLICATIONS

This application claims priority to Plant Breeders' Right Application Number 2017/2620, which was filed at Community Plant Variety Office in the European Union on Oct. 18, 2017, the contents of which are hereby incorporated by reference for all purposes.

Botanical/commercial classification:
Latin name—*Rosa hybrida.*
Common name—Miniature Rose Plant.
Varietal denomination: 'KORpot083'.

SUMMARY OF THE INVENTION

The new variety of *Rosa hybrida* Miniature Rose Plant of the present invention was created during 2014 at Offenseth-Sparrieshoop, Germany by artificial pollination wherein two parents were crossed which previously had been studied in the hope that they would contribute the desired characteristics. The female parent (i.e., seed parent) of the new variety was an unnamed seedling from a previous cross of the 'KORpolare' variety (U.S. Plant Pat. No. 18,840) and an unnamed seedling. The male parent (i.e., pollen parent) of the new variety was the 'INTERtroning' variety (non-patented in the United States).

The parentage can be summarized as follows:

('KORpolare' x unnamed seedling) x 'INTERtroning'

The seeds resulting from the above pollination were sown and small plants were obtained which were physically and biologically different from each other. Selective study resulted in the identification of a single plant of the new variety.

It was found that the new Miniature Rose Plant of the present invention possesses the following combination of characteristics:

(a) abundantly and substantially continuously forms attractive, red and white striped colored blossoms,
(b) exhibits a compact growth habit,
(c) forms vigorous vegetation, and
(d) forms attractive ornamental foliage with good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the ('KORpolare' x unnamed seedling) variety (i.e., seed parent) exhibits a lower petal count compared to the new variety and a red flower color, whereas the new variety exhibits red and white striped flowers and has an improved shelf life compared to the seed parent. Additionally, the 'INTERtroning' variety (i.e., pollen parent) exhibits a larger flower size and a less compact growth habit compared to the new variety and the new variety has an improved shelf life compared to the pollen parent. Moreover, the 'Poulpah101' variety exhibits pinkishred/white striped semi-double flowers, whereas the new variety exhibits red/white striped double flowers and displays a more compact growth habit and smaller flower size than the 'Poulpah101' variety.

The new variety has been found to undergo asexual propagation in Klein Offenseth-Sparrieshoop, Germany by a number of routes such as vegetative cuttings. Asexual propagation techniques in Germany have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot083'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Klein Offenseth-Sparrieshoop, Germany while growing indoors on its own roots in a 10.5 cm container.

FIG. 1—illustrates a specimen of a plant displaying floral buds and flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during July, while growing in a one-gallon container on its own roots in a greenhouse in Cochranville, Pa.

Class: Miniature Rose Plant.

Plant:

*Habit*.—Compact, very bushy and upright.

*Height*.—Approximately 35.0 cm on average.

*Width*.—Approximately 32.0 cm on average.

Branches:

*Stem color*.—Commonly near Green Group 138A.

*Stem length*.—Approximately 35.0 cm on average.

*Stem diameter*.—Approximately 3.0 mm on average.

*Thorns*.—Young thorns: moderate amount; length is approximately 5.0 mm on average, width is approximately 2.0 mm at point of attachment on average, and color is commonly near Orange-Red Group 35C at the point of attachment transitioning to Yellow Group 4B at the apex. Old thorns: moderate amount; length is approximately 6.0 mm on average, width is approximately 5.0 mm at point of attachment on average, and mostly color is commonly near Yellow Group 4B with some blending of near Orange-Red Group 35C. Shape: concave.

Foliage:

*General appearance*.—Ornamental with good disease resistance.

*Young foliage*.—Upper surface color: commonly near Green Group 138A. Under surface color: commonly near Green Group 138B.

*Old foliage*.—Upper surface color: commonly near Group NN137A. Under surface color: commonly near Green Group 137B.

*Petioles*.—Upper surface: texture is smooth, color is commonly near Green Group 137B. Under surface: texture is smooth, color is commonly near Green Group 137D. Diameter: approximately 1.0 mm on average. Length of terminal leaflet: approximately 4.2 cm on average.

*Petiolues*.—Color: commonly near Green Group 143A. Length: approximately 1.0 mm on average. Width: approximately 1.0 mm on average.

*Rachis*.—Color: upper surface is commonly near Green Group 137B, under surface is commonly near Green Group 137D. Size: length is approximately 3.0 cm on average; and diameter is commonly near 1.0 mm on average.

*Stipules*.—Length: approximately 17.0 mm on average. Width: approximately 5.0 mm on average. Margin: entire to erose. Shape: apex is apiculate and base is flat. Color: upper surface is commonly near Green Group 137C; lower surface is commonly near Green Group 137D.

*Leaf margin*.—Serrate.

*Leaf arrangement*.—Odd pinnate.

Leaflets:

*Number*.—3, 5, and 7.

*Shape*.—Ovate; apex is acute; and base is rounded.

*Venation*.—Pattern is reticulate and color is commonly near Green Group 143A.

*Texture*.—upper surface is smooth; under surface is smooth.

*Size*.—Terminal leaflet: length is approximately 4.5 cm on average and width is approximately 2.3 cm on average. Lower leaflets: length is approximately 2.7 cm on average and width is approximately 1.7 cm on average. 5-Leaflet leaf: length is approximately 9.5 cm on average and width is approximately 7.0 cm on average.

Inflorescence:

*Number of flowers*.—Approximately 13 blooms on average on a plant at once.

*Number of blooms per stem or in a cluster*.—Commonly between 3 and 5 blooms per stem on average.

*Peducle*.—Color: commonly Yellow-Green Group 144A. Diameter: approximately 3.0 mm on average. Length: approximately 3.2 cm on average. Surface texture: sparely glandular.

*Sepals*.—Number: commonly 5. Upper surface color and texture: covered in short pubescence and color is commonly near Yellow-Green Group 144A. Under surface color and texture: puberulent and color is commonly near Yellow-Green Group 144B. Size: length is approximately 2.8 cm on average and width is approximately 7.0 mm on average. Arrangement: arranged evenly around the top of the receptacle and reflexed away from the base of the corolla. Shape: lanceolate; apex is acute to aristate. Margin: entire with occasional extensions on one or two sepals measuring approximately 5.0 mm in length and less than 1.0 mm in width.

*Bud*.—Shape: ovoid. Size: length is approximately 1.5 cm on average; width is approximately 1.3 cm on average. Color (when opening): commonly near Red Group 53C with some striping of near Red Group 54D.

*Flower*.—Red and white striped colored. Form: double, flat to cuplike. Diameter: approximately 3.5 cm on average. Height: approximately 2.0 cm on average. Duration: commonly on the plant 19 to 20 days. Color upon opening: commonly near Red Group N45A with a basal petal spot of near White Group 155B; most of the petals exhibit striping of both near White Group 155B and near Red Group 54D. Color after opening: commonly near Red Group N45A with a basal petal spot of near White Group 155B; most of the petals exhibit striping of both near White Group 155B and near Red Group 54D; the apices and margins of the petals begin to burn and turn a color between Greyed-Purple Group 187A and Greyed-Purple Group N187A.

*Fragrance*.—None noticeable.

*Petal*.—Number: approximately 26 on average. Drop: good. Size: length is approximately 2.0 cm on average and width is approximately 1.8 cm on average. Shape: overall shape is broadly obovate; apex shape is round; and base shape is cuneate. Margin: entire. Arrangement: rosulate.

*Petaloids*.—Number: approximately 5 per flower on average. Arrangement: rosulate. Color: some petaloids are primarily near Red Group N45A and near White Group 155B at the point of attachment; some are primarily near White Group 155B blended with near Red Group 54D and speckled or striated with near Red Group N45A; and the color patterning is variable. Size: length is approximately 1.0 cm on average and width is approximately 5.0 mm on average. Margins: variable, entire to erose. Shape: overall shape is variable, oblong to spatulate, with some petaloids highly irregular; apex is variable, mostly round, and base is cuneate.

*Stamen*.—Number: approximately 80 on average. Anthers: number is about 80 and color is commonly near Greyed-Orange Group 163B; length is approximately 2.0 mm on average and width is approximately 1.0 mm on average. Filaments: length is approximately 3.0 mm on average and color is commonly near Greyed-Yellow Group 160C.

*Pistils*.—Arrangement: separate and free. Number: approximately 34 on average. Style: color is commonly near Yellow-White Group 158B; and length is approximately 1.0 cm on average. Stigma: color is commonly near Yellow-White Group 158A; diameter is commonly less than 1.0 mm on average; position in relation to the anthers is slightly inferior in position to the anthers.

*Receptacle*.—Achenes stand on the bottom and wall; diameter is approximately 8.0 mm on average, depth is approximately 7.0 mm on average, shape is oval, color is commonly near Yellow-Green Group 144A, and surface texture is smooth.

*Pollen*.—None observed.

*Hips/seed*.—None observed.

Development:

*Vegetation*.—Dark green, vigorous, and strong.

*Blooming*.—Abundant and substantially continuous.

*Winter hardiness*.—Unknown.

*Resistance to disease*.—Good resistance to Powdery mildew, including *Sphaerotheca pannosa*, and *Botrytis* (*Botrytis cinerea*) disease under normal greenhouse growing conditions in Cochranville, Pa.

Plants of the 'KORpot083' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) abundantly and substantially continuously forms attractive, red and white striped colored blossoms, (b) exhibits a compact growth habit, (c) forms vigorous vegetation, and (d) forms attractive ornamental foliage with good disease resistance;

substantially as herein shown and described.

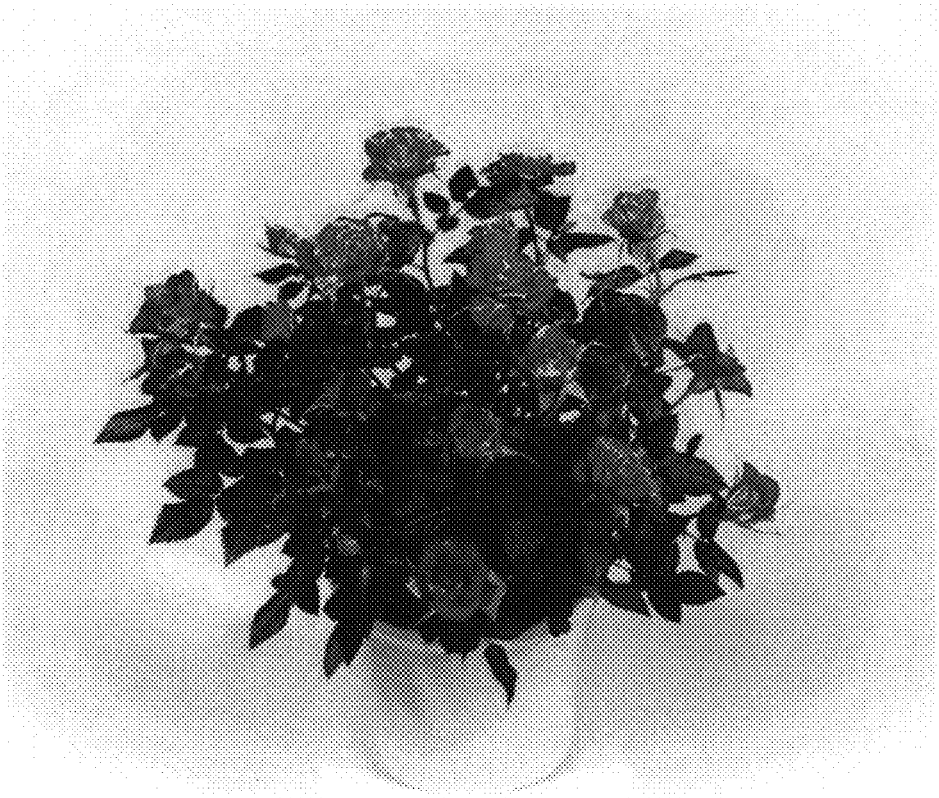

* * * * *